(12) United States Patent
Esser et al.

(10) Patent No.: US 7,183,420 B2
(45) Date of Patent: Feb. 27, 2007

(54) METHOD FOR THE PREPARATION OF 11(12)-PENTADECEN-15-OLIDES

(75) Inventors: Peter Esser, Summerville, SC (US); Oskar Koch, Göttingen (DE); Werner Marks, Brevörde (DE); Jared Klein, Summerville, SC (US)

(73) Assignee: Symrise GmbH & Co. KG, Holzminden (DE)

( * ) Notice: Subject to any disclaimer, the term of this patent is extended or adjusted under 35 U.S.C. 154(b) by 479 days.

(21) Appl. No.: 10/463,872

(22) Filed: Jun. 18, 2003

(65) Prior Publication Data

US 2004/0030194 A1 Feb. 12, 2004

(30) Foreign Application Priority Data

Jun. 19, 2002 (DE) ................................ 102 27 483

(51) Int. Cl.
*C07D 313/00* (2006.01)
(52) U.S. Cl. ..................................................... 549/266
(58) Field of Classification Search ................ 514/475; 549/531, 266
See application file for complete search history.

(56) References Cited

U.S. PATENT DOCUMENTS 3,890,353 A * 6/1975 Becker ........................ 549/266
2005/0085536 A1* 4/2005 Lambrecht et al. .......... 514/475

FOREIGN PATENT DOCUMENTS

| EP | 0 503 312 A1 | 9/1992 |
|----|--------------|--------|
| EP | 0 862 911 A2 | 9/1998 |
| FR | 2 043 784 | 2/1971 |
| FR | 0 424 787 | 5/1991 |
| WO | WO 97/32948 | 9/1997 |

OTHER PUBLICATIONS

Yu N. Ogibin et al., Ring Expansion Reaction Of 1-Hydroperoxy-16-Oxabicyclo[10.4.0] Hexadecane Catalyzed By Copper Ions: Use In The Synthesis of 15-Pentadecanolide.

* cited by examiner

*Primary Examiner*—Margaret D. Seaman
*Assistant Examiner*—Niloofar Rahmani
(74) *Attorney, Agent, or Firm*—Roylance, Abrams, Berdo & Goodman, L.L.P.

(57) ABSTRACT

The invention relates to an improved method for the preparation of 11(12)-pentadecen-15-olides.

18 Claims, No Drawings

METHOD FOR THE PREPARATION OF 11(12)-PENTADECEN-15-OLIDES

The invention relates to an improved method of preparation for 11(12)-pentadecen-15-olides.

The macrocyclic lactones 11-pentadecen-15-olide (=15-hydroxypentadec-11-enoic acid lactone) and 12-pentadecen-15-olide (=15-hydroxypentadec-12-enoic acid lactone) and their mixtures (11(12)-pentadecen-15-olides) are known musk perfumes. In this context both the particular (E)- and also (Z)-forms as well as mixtures thereof are of interest from the fragrance standpoint. The fragrance characteristics of these substances are described in EP-A 424 787. It is also adequately known that 15-penta-decanolide (15-hydroxypentadecanoic acid lactone), which is also used as a musk perfume, can be obtained from the 11(12)-pentadecen-15-olides by means of hydrogenation.

The preparation of 11(12)-pentadecen-15-olides is known per se. The most important methods of preparation at present use 13-oxabicyclo[10.4.0]hexadec-1(12)-ene (DDP) as starting material. 1-hydroperoxy-16-oxabicyclo[10.4.0]hexadecane (DDP-OOH) is obtained by means of acid-catalysed addition of hydrogen peroxide to DDP. The cleavage of the DDP-OOH with the formation of the macrocyclic ring is to be regarded as the decisive step in the synthesis to give the 11(12)-pentadecen-15-olides. This cleavage is usually carried out in the presence of catalysts such as $Cu(OAc)_2$ and optionally $FeSO_4$. If this reaction step is carried out using heat only, the reaction product contains considerable amounts of the saturated compound 15-pentadecanolide which, however, although it is a musk perfume has different fragrance characteristics to 11(12)-pentadecen-15-olides and therefore should be formed only in the smallest amounts possible. Moreover, when the cleavage is carried out by means of heat only, a high residue formation (for example distillation sump) is disadvantageous.

DDP is usually obtained by acid-catalysed cyclisation of 2-(3-hydroxypropyl)-1-cyclododecanone (OCP) with elimination of water, which OCP, in turn, can be synthesised by free radical addition of allyl alcohol to cyclododecanone (for example in DE-OS 2 136 496).

The process for the preparation of the 11(12)-pentadecen-15-olides can be illustrated by the following scheme:

In EP-A 424 787 OCP was homogenised in 4.6 equivalents by weight of glacial acetic acid at ambient temperature, a cold 25% aqueous solution of sulphuric acid (approximately 51% (mol) (approximately 21% (m/m)) based on OCP) was added and the reaction mixture was then cooled to 0° C. 1.65 molar equivalents of hydrogen peroxide (70% solution) were then added, the temperature rising to 7° C. After a brief post-reaction time the solid formed (DDP-OOH) was filtered off and this was washed with water and aqueous $NaHCO_3$ solution and dried; the yield was 80%.

Cleavage of the DDP-OOH was carried out by introducing the DDP-OOH in portions into a saturated solution of $Cu(OAc)_2$ in methanol (prepared from approximately 94% (mol) $Cu(OAc)_2$ and 12.3 parts by weight methanol based on the DDP-OOH; the concentration of DDP-OOH in this amount of methanol was approximately 0.25 mol/l). The addition of two portions of $FeSO_4$ (each of only just 20% (mol) based on DDP-OOH) and stirring overnight at ambient temperature followed. For working up, the mixture was poured onto saturated aqueous NaCl solution, extracted with diisopropyl ether and this extract was washed with saturated aqueous $NaHCO_3$ solution and saturated aqueous NaCl solution. After drying and fractional distillation, 73% of the theoretical yield of 11(12)-pentadecen-15-olides, which still contained 8% 15-pentadecanolide, was obtained.

In Russ. Chem. Bull. 1998, 47, 1166–1169 DDP was initially introduced into 5.2 equivalents by weight of glacial acetic acid at 0° C. and a mixture consisting of a 50% aqueous solution of sulphuric acid (approximately 26% (mol) (=11% (m/m)), based on DDP) and 30% hydrogen peroxide (approximately 1.89 molar equivalents) was added. After a brief post-reaction time, the solid formed (DDP-OOH) was filtered off and this was washed with a 50% acetic acid solution (80% (m/m), based on DDP) and then several times with water (4 washing operations each with 2 parts by weight of water, based on DDP) until the wash water was neutral. After drying the solid, 85% of the theoretical yield of DDP-OOH, which had a 96% purity, was obtained.

Cleavage of the DDP-OOH was carried out by metering a suspension of 1 part DDP-OOH and approximately 3.8

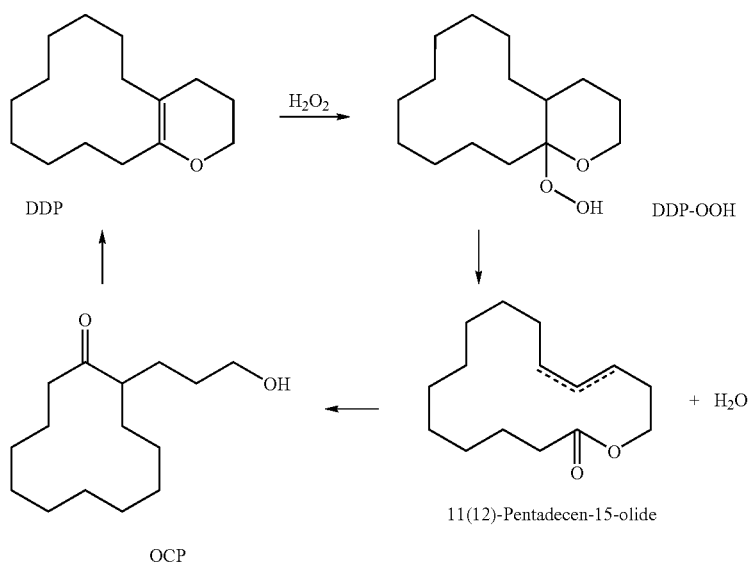

parts by weight 4-methylpentan-2-one (MIBK) over a prolonged period into a boiling solution of Cu(OAc)₂ in approximately 3.8 parts by weight MIBK (based on DDP-OOH). The amount of Cu(OAc)₂ was varied in the range from 0.15 to 7.0% (mol), based on the DDP-OOH, the optimum being 5% (mol) Cu(OAc)₂ according to the authors. After 3 hours of post-reaction time at the boil, the reaction mixture was cooled and the precipitated copper salts were filtered off. The filtrate was washed with hot water (2 washing operations, each with 7.7 equivalents by weight of water based on DDP-OOH) and concentrated. Using 5% (mol) Cu(OAc)₂, a crude yield of 11(12)-pentadecen-15-olides of 96.5% of the theoretical yield was obtained.

Disadvantages of this method are, in particular, the precipitation of elementary copper and/or insoluble copper compounds under the reaction conditions for the cleavage of DDP-OOH and also the large amounts of reagents and auxiliaries used in the reactions. Further disadvantages which may be mentioned are, for example, the numerous, in some cases time-consuming, process steps and washing operations and the associated environmental and safety aspects as well as poor space-time yields. An additional disadvantage when the scale of the last-mentioned method is increased is that substantial amounts of ring-constricted lactones with a ω-hydroxyalkyl side chain are formed.

The known synthesis methods are therefore unsuitable for an industrial reaction. An industrial method that yields 11(12)-pentadecen-15-olides in a simple and inexpensive manner is therefore of great commercial interest.

By means of the present invention it is possible to overcome the disadvantages mentioned and to provide an industrially advantageous method. The method according to the invention is particularly suitable for use on an industrial scale.

The subject of the present invention is therefore a method for the preparation of 11(12)-pentadecen-15-olides using DDP-OOH as the starting material in the presence of a Cu(II) compound and a diluent, characterised in that an azeotrope containing water and diluent is distilled off during the reaction.

Cu(II) compounds that are advantageous according to the invention are those that are soluble in the solvent used under the reaction conditions of the DDP-OOH reaction. Such Cu(II) compounds have a solubility in the diluent at 20° C. of at least 0.5 g/kg diluent, preferably of at least 1 g/kg. The Cu(II) compounds can be used in the anhydrous form or in the form of hydrates (water of crystallisation). The amount of water in the water of crystallisation is not critical.

Preferred Cu(II) compounds are those containing organic radicals. In addition to Cu(II) 2,4-pentanedionate derivatives, Cu(II) carboxylates are particularly suitable in this regard. Preferred Cu(II) 2,4-pentanedionates are Cu(II) acetylacetonate, Cu(II) 1,1,1-trifluoroacetylacetonate and [bis(2,2,6,6-tetramethyl-3,5-heptanedionato)]-Cu(II). Cu(II) carboxylates of alkylcarboxylic acids having 2 to 5 carbon atoms, in particular Cu(II) acetate and Cu(II)-propionate, are particularly preferred.

According to the invention one or more Cu(II) compounds can be used. The amount of the Cu(II) compounds that is advantageous according to the invention in the conversion of DDP-OOH to the 11(12)-pentadecen-15-olides is 0.02 to 1.5% (mol), based on DDP-OOH, preferably 0.05 to 1% (mol) and particularly preferentially 0.1 to 0.6% (mol).

All liquid organic compounds that form azeotropes with water can be used as diluents. According to the invention these diluents act as water entrainers during the distillative removal of the diluent. One or more diluents can be used; the use of only one diluent is preferred. Advantageous diluents have a boiling point in the range of 70 to 230° C., and particularly advantageously in the range from 90 to 150° C., under normal pressure. Preferred diluents are aliphatic esters, ethers or ketones, in particular ketones. The preferred ester is butyl acetate and the preferred ether is di-n-butyl ether. Preferred ketones are 2-pentanone, 3-pentanone, 4-methylpentan-2-one (MIBK), ethyl isopropyl ketone and diisopropyl ketone; MIBK is particularly preferred.

It is preferred to remove the water from the azeotrope distilled off during the cleavage and to re-use the diluent for the cleavage. In this context it is advantageous if this recovered diluent has an acid number of less than or equal to 3 mg KOH/g. The acid number corresponds to the number of milligrams of potassium hydroxide that are needed to neutralise 1 gram of the recovered diluent.

The weight ratio of DDP-OOH to the total amount of the diluent used in the cleavage that is preferred according to the invention is in the range of 1:2 to 1:7, preferably 1:3 to 1:5.

The temperature range in which the cleavage is carried out is 70 to 120° C. The cleavage is preferably carried out at temperatures in the range of 80 to 100° C., particularly preferentially at 85 to 95° C.

The advantageous pressure range in which the cleavage is carried out is 0.01 mbar to 2 bar. The method is preferably carried out at pressures below 1013 mbar, in particular in the range from 50 to 800 mbar. If the reaction takes place discontinuously, the pressure is preferably lowered ever further as cleavage progresses and the temperature of cleavage is kept substantially constant, preferably starting at 450 to 750 mbar and ending at 100 to 400 mbar.

The DDP-OOH used in the cleavage can be anhydrous or can contain water; preferred DDP-OOH contains water. The water content of the DDP-OOH is advantageously in the range from 5 to 40% (m/m), preferably 10 to 30% (m/m) and particularly preferentially 15 to 25% (m/m).

Surprisingly, it has also been found that certain additives suppress precipitation of copper and/or insoluble copper compounds during the cleavage. The conversion of DDP-OOH to the 11(12)-pentadecen-15-olides is preferably carried out in the presence of additives which can be represented by the following formula:

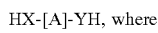

HX-[A]-YH, where

X and Y independently of one another denote O or N-R, where R=H or an organic radical having 1 to 10 carbon atoms, and A is an organic radical containing 2 to 100 carbon atoms.

Advantageously the boiling point of the additive is above the boiling point of the diluent used and above [lacuna] of the azeotropic mixture of diluent and water.

Preferably A contains 6 to 50 carbon atoms, particularly preferentially 10 to 30 carbon atoms. The radical R preferably contains 1 to 4 carbon atoms; R is preferably methyl or ethyl.

The organic radical A preferably contains the heteroatoms O or N, preferably in the form of hydroxyl groups, ether groups, or amino groups; ether groups and secondary amino groups are preferred. One or more organic groups can be attached to the carbon skeleton of the radical A, which groups independently of one another can be straight-chain, branched, cyclic, heterocyclic, aromatic or hetero-aromatic, the groups containing hetero-atoms preferably being those containing O or N.

Advantageous additives are $\alpha,\omega$-diols and $\alpha,\omega$-amino alcohols.

In a particularly advantageous embodiment additives are employed which contain exclusively oxygen as hetero-atoms. These $\alpha,\omega$-diols preferably contain at least 2 oxygen atoms, preferably in the form of ether groups, in the carbon skeleton of the organic radical A.

Particularly preferred additives are polyalkylene glycols, in particular polyethylene glycols (PEG), polypropylene glycols or polytetramethylene glycols (polytetrahydrofurans), which at least have a degree of polymerisation of 2 and preferably have molar masses in the range of 144 to approximately 2,200. At higher molar masses the polyalkylene glycols are polydisperse and have a molar mass range, for example PEG 1000 typically has a molar mass range of 950 to 1,050. Polyethylene glycols (PEG) with degrees of polymerisation of 4 to 50 are very particularly preferred. PEG 200 to PEG 1000, and here, in turn, PEG 400, PEG 600 and PEG 800, are preferred to a particular extent. These products are commercially available.

According to the invention one or more additives can be used. The quantity of the additives that is advantageous according to the invention when converting DDP-OOH to the 11(12)-pentadecen-15-olides is 0.5 to 15% (m/m), based on the DDP-OOH, preferably 1 to 10% (m/m) particularly preferentially 2 to 8% (m/m) and very particularly preferentially 3 to 6% (m/m).

The cleavage is preferably carried out in such a way that a mixture containing diluent and Cu(II) compound as well as, optionally, additive is initially introduced and heated. A suspension or solution containing diluent and DDP-OOH is then added to this heated mixture. It is particularly advantageous to start the azeotropic distillative removal of the aqueous diluent at the start of metering of the DDP-OOH.

When cleavage is complete, it is advantageous very substantially to deactivate the copper ions before isolation of the 11(12)-pentadecen-15-olides by distillation. For this purpose it is appropriate to complex the copper to a substantial extent and/or to precipitate it as a copper compound. Strong complexing agents for copper, such as, for example, cryptans, EDTA or citric acid, are particularly suitable for this purpose.

The cleavage can be carried out discontinuously, semi-continuously or continuously; the semi-continuous or continuous procedure is preferred.

The cleavage can also be carried out in a continuously operated stirred vessel reactor. In this case, preferably not only is a suspension of the DDP-OOH and diluent metered, but, in parallel, a suspension of a Cu(II) compound, diluent and, optionally, an added additive. The crude suspension removed from the stirred vessel reactor is advantageously also allowed to run through a second, continuously operated stirred vessel reactor, in which further aqueous diluent is distilled off, for post-reaction. If required, a strong Cu complexing agent can be metered into a third, continuously operated stirred vessel reactor and the distillation of the aqueous diluent continued. The outflow from this stirred vessel reactor can be fed to a continuously operated distillation column, in which diluent and residual water is removed via the top and a diluent-free crude product is obtained as bottom product. If a strong Cu complexing agent has been added, the Cu complex that may have precipitated can be filtered off and the crude 11(12)-pentadecen-15-olides further purified as required.

Whether the method is carried out continuously, semi-continuously or discontinuously, the 11(12)-pentadecen-15-olides are typically obtained in an isolated yield of 97% of theory in the cleavage reaction and of 87% of theory over all steps starting from DDP.

A further subject of the present invention is a method for the preparation of DDP-OOH using DDP and hydrogen peroxide as starting materials in the presence of acetic acid and sulphuric acid, characterised in that the reaction is carried out in the presence of 0.05 to 5% (mol) $H_2SO_4$, based on DDP.

The amount of $H_2SO_4$ preferred according to the invention for the conversion of DDP to DDP-OOH is 0.1 to 3% (mol), based on DDP, and particularly preferentially 0.2 to 2.5% (mol).

The weight ratio of DDP to acetic acid preferred according to the invention is in the range of 1:2 to 1:8, preferably 1:4 to 1:6.

For a spontaneous and uniform course of reaction, it is advantageous initially to introduce a portion of the previous crude batch (crude reaction product mixture that has not been filtered and may still contain DDP-OOH crystals, the main constituent of which is acetic acid).

Hydrogen peroxide of various strengths can be used for the addition $H_2O_2$ to DDP to give DDP-OOH. Typically 30 to 70% aqueous hydrogen peroxide is used; 50 or 70% is preferred.

The amount of $H_2O_2$ preferred according to the invention is 0.8 to 1.25 molar equivalents, based on DDP, and particularly preferentially 0.95 to 1.1 molar equivalents.

The temperature range in which the addition of $H_2O_2$ is carried out is from 0 to 10° C., preferably 3 to 8° C. A reaction temperature of around 5° C. proves particularly suitable.

OCP can also be used as starting material for the preparation of DDP-OOH. In this case it can then be advantageous to use more acetic acid, typically 10 to 30% (m/m) more than when DDP is used as educt.

When the reaction is complete, the reaction mixture is filtered and the DDP-OOH crystals washed with as little water as possible in order substantially to free the crystals from acetic acid and sulphuric acid. Two counter-current washes with water, in each case with twice the amount by weight of water, based on DDP-OOH, is advantageous. Belt filters and horizontal centrifuges are particularly suitable for this filtration. Water (for example demineralised or distilled) and/or wash water from previous DDP-OOH crystal washes are preferably used for the washing operations. It is particularly advantageous not to dry further the DDP-OOH crystals obtained after filtration and the washing operations but to maintain the water content obtained.

The filtrate (crystal-free reaction solution) obtained after filtering off the DDP-OOH crystals and the subsequent washing operations contains mainly acetic acid. The water content in this filtrate is usually 10 to 25% (m/m). This filtrate is preferably re-used for the same reaction, usually after the addition of a portion of fresh glacial acetic acid.

The washing operations and the filtration and the drying of the washed DDP-OOH crystals that is optionally carried out should take place under conditions that are as gentle as possible and at temperatures in the range from −10 to +10° C.; a temperature of around 0° C. is preferred.

The DDP-OOH crystals that are obtained after filtration, washing operations and optionally drying preferably have a water content of 5 to 40% (m/m), particularly preferentially of 10 to 30% (m/m) and very particularly preferentially of 15 to 25% (m/m).

The preparation of DDP-OOH can be carried out discontinuously, semi-continuously or continuously.

The reaction can, for example, be carried out in a continuously operated stirred vessel reactor. Hydrogen peroxide, on the one hand, and, in parallel, a mixture containing DDP, acetic acid, sulphuric acid and water, on the other hand, is then metered into this stirred vessel reactor. This mixture can also be prepared from DDP, crystal-free reaction solution (for example from the previous batch), some fresh sulphuric acid and fresh acetic acid and, if appropriate, water. If the suspension withdrawn from the stirred vessel reactor is also allowed to run through a second, continuously operated stirred vessel reactor for post-reaction, the continuous procedure does not differ from the discontinuous (batch) variant in respect of yield and quality of the product.

Whether in the method carried out continuously, semi-continuously or discontinuously, DDP-OOH is typically obtained in an isolated yield of 90% of theory, starting from DDP.

It is advisable to carry out all steps in the preparation of the 11(12)-pentadecen-15-olides, in particular the preparation, filtration and handling of the DDP-OOH crystals, in an atmosphere of blanketing gas or mixtures of blanketing gases. Particularly suitable blanketing gases are, for example, nitrogen, argon, helium or carbon dioxide.

The fact that the reaction of DDP with hydrogen peroxide to give DDP-OOH can be carried out continuously, the separation of reaction solution and DDP-OOH crystal and the purification thereof can be carried out quasi-continuously and the rearrangement of DDP-OOH under copper(11) catalysis to give the 11(12)-pentadecen-15-olides can likewise be carried out continuously is important not only from the standpoint of economic aspects. From the standpoint of the aspect of safety at work and for the environment, the amount of hydroperoxides present in the process can be reduced to a minimum in this way.

By means of the present invention it is possible to close the solvent and catalyst circuits and to reduce waste to a minimum.

The following examples illustrate the invention.

EXAMPLE 1

Preparation of DDP-OOH 448 g DDP, 2070 g acetic acid, 330 g demineralised water and 4 g sulphuric acid thermostat-controlled at 5° C. were initially introduced into a 6 l double-walled vessel with a bottom outlet, provided with a paddle stirrer, two metering pumps, peristaltic pump, cryostat and nitrogen connection. The mixture was stirred at 400 rpm (revolutions per minute). 140 g 50% hydrogen peroxide were metered in in the course of 30 minutes. The reaction was exothermic and spontaneous. After a post-reaction time of 15 minutes, the reaction mixture was filtered through a porcelain suction filter and washed twice, using 1000 g water each time (the combined filtrates form the crystal-free reaction solution). The yield of DDP-OOH (without water content of approximately 17% (m/m)) was 89% of theory.

EXAMPLE 2

Preparation of DDP-OOH 2600 g crystal-free reaction solution from the previous batch (from Example 1), 448 g DDP, 180 g acetic acid and 0.4 g sulphuric acid thermostat-controlled at 5° C. were initially introduced into a 6 l double-walled vessel with a bottom outlet, provided with a paddle stirrer, metering pump, cryostat and nitrogen connection. The mixture was stirred at 400 rpm. 100 g 70% hydrogen peroxide were metered in in the course of 30 minutes. The reaction was exothermic and spontaneous. The post-reaction time was 15 minutes. 300 g of the crude reaction product mixture remained for the subsequent batch in the reactor. The other 3000 g were fed for further purification.

EXAMPLE 3

Continuous Preparation of DDP-OOH 300 g of the previous crude batch (unfiltered crude reaction product mixture still containing DDP and OOH crystals), 448 g DDP, 2070 g acetic acid, 330 g demineralised water and 4 g sulphuric acid thermostat-controlled at 5° C. were initially introduced into a 6 l double-walled vessel with bottom outlet, equipped with a paddle stirrer, two metering pumps, peristaltic pump, cryostat and nitrogen connection. The mixture was stirred at 400 rpm. 140 g 50% hydrogen peroxide were metered in in the course of 30 minutes. The reaction was exothermic and spontaneous. After 15 minutes, the reaction was continued continuously in that, using two metering pumps, 70% hydrogen peroxide in the one pump and a metering mixture of crystal-free reaction solution, DDP, acetic acid and sulphuric acid, in the other pump, were introduced in parallel into the reaction vessel. At the same time reaction solution was withdrawn by means of a peristaltic pump via the bottom outlet. 70% hydrogen peroxide was metered in at a rate of 200 g/h. The metering mixture was prepared in a ratio of 2300 g crystal-free reaction solution, 448 g DDP, 180 g acetic acid and 0.4 g sulphuric acid and metered in at a rate of 5857 g/h. The reaction solution was withdrawn at a rate of approximately 6057 g/h in such a way that the liquid level in the reactor remained substantially constant. The crude batch was fed for filtration and further purification.

EXAMPLE 4

Filtration of DDP-OOH

A horizontal centrifuge was used to separate the DDP-OOH crystals from the mother liquor. This was cooled to approximately +5° C. and rendered inert with nitrogen before the start of the centrifuging process. The centrifuge was set at a centrifuging speed of revolution of 2300 rpm. 15 kg of the reaction solution were pumped in in the course of 1 to 1.5 minutes using a peristaltic pump. The feed line was flushed with 2 kg crystal-free reaction solution. Centrifuging at 2300 rpm was carried out for 5 minutes. 13.9 kg crystal-free reaction solution was obtained, which was thermostatically controlled to 1° C. for further use. After reducing the centrifuging speed of revolution to 600 rpm the centrifuge was emptied by reverse drawing. 3.1 kg moist crystals of DDP-OOH were obtained.

The crystals were mashed with 6.9 kg wash water at approximately 1° C. and the mash was stirred vigorously for 15 minutes. Demineralised water or the filtrate from previous filtration batches (acetic acid content approximately 3% (m/m)) can be used as wash water.

The horizontal centrifuge was set at a centrifuging speed of revolution of 2600 rpm. 10 kg DDP-OOH suspension were metered in in the course of 1 minute using a peristaltic pump. Intermediate centrifuging at an unchanged speed of revolution was carried our for a further 1 minute. 6.1 kg waste water was obtained, which was discarded. At the same speed of revolution, washing was carried out with 5.9 kg demineralised water, which had been pre-cooled to 1° C. and was pumped in in the course of 1 minute using a metering pump. The mixture was then centrifuged for 10 minutes at 2600 rpm. 6.9 kg wash water was obtained (that will be re-used in the following batch). At the end of centrifuging, the centrifuging speed of revolution was reduced to 600 rpm. The centrifuge was emptied by reverse drawing. 2.9 kg DDP-OHH (sic) crystals with a moisture content of approximately 20% were obtained, which corresponds to an amount of 2.30 kg DDP-OOH. The yield was thus 90% of theory, based on DDP comprising the steps of DDP-OOH formation and the isolation thereof. The product was virtually free from acetic acid and sulphuric acid.

EXAMPLE 5

Preparation of 11 (12)-Pentadecen-15-olides

A mixture of 800 g MIBK, 100 g PEG 400 and 3.6 g copper II acetate monohydrate was initially introduced into a 6 l double-walled vessel that had been rendered inert with hydrogen and was equipped with a stirrer, thermostat, distillation column, column head, vacuum pump and vacuum control. The mixture was heated and boiled under reflux for 30 minutes (top temperature approximately 112° C., bottom temperature approximately 118° C.). A vacuum of 550 mbar was set with care, so that a bottom temperature of 90° C. and a top temperature of 85° C. were established.

2.9 kg of the DDP-OOH (moist, approx. 20% (m/m) water, from Example 4) and 9 kg MIBK (optionally MIBK recovered from the DDP-OOH cleavage) were mashed in a metering vessel, with stirrer, which was thermostat-controlled at 0° C. Approximately 2 l/h of this suspension was introduced from the metering vessel into the 6 l double-walled vessel by means of a peristaltic pump. At the start of metering somewhat less MIBK was withdrawn at the top of the column than was metered into the double-walled vessel with the suspension. Azeotropic distillation was continued until no further water separated off. In this way 8 kg MIBK (acid number 2.0 mg KOH/g) and approximately 600 g water had been distilled off at the end of metering. The MIBK can advantageously be re-used. In order to keep the bottom temperature at approximately 90° C., the vacuum was lowered to about 350 mbar in the course of metering. The top temperature fell to about 70° C. when the vacuum was lowered.

After termination of the distillation, the heating was switched off and the vessel was charged with nitrogen gas. After adding 5 g citric acid, the mixture was heated, with stirring, under normal pressure and distilled until no further water separated off. The bottom temperature was then approximately 120° C. and the top temperature approximately 115° C. The distillation was continued applying vacuum with caution. distillation was discontinued and the vessel was charged with nitrogen gas. The distillate obtained consisted of approximately 30 g water and 1.6 kg MIBK. At 50° C. to 60° C., the crude product was filtered off through a porcelain suction filter and washed twice with 100 g MIBK. The filtrate and the two wash filtrates were collected separately. 2250 g filtrate and 6.2 g dry copper citrate, as well as approximately 250 g wash filtrates, were obtained. It was possible to recover a further 50 g filtrate from the wash filtrates by concentration.

Following renewed distillation, 40 g first runnings; 2080 g 11(12)-pentadecen-15-olides and 150 g distillation residues, which, inter alia, contain the PEG 400, were obtained. This corresponds to a yield of 11(12)-pentadecen-15-olides of 87% of theory over all steps starting from DDP and a yield of 97% of theory for the step from DDP-OOH to the 11 (12)-pentadecen-15-olides.

EXAMPLE 6

Continuous Preparation of 11(12)-Pentadecen-15-olides

The procedure is as in Example 5 up to the end of metering and the point of azeotropic distillation at which 8 kg MIBK and approximately 600 g water had been distilled off.

At this point the reaction was continued continuously in that a DDP-OOH suspension continued to be metered in via the peristaltic pump, a second metering mixture was metered in via a second metering pump and reaction solution was continuously withdrawn via the bottom outlet via a third peristaltic pump. The DDP-OOH suspension was prepared in a ratio of 2.9 kg DDP-OOH (moist, approx. 20% (m/m) water, from Example 4) to 9 kg MIBK and metered at a metering rate of 1.7 kg/h. The second metering mixture was prepared from 800 g MIBK, 100 g PEG 400 and 3.6 g $Cu(OAc)_2$ monohydrate and used as a very well stirred suspension preheated to 110° C. This second metering mixture was metered at a metering rate of 130 g/h. 1230 g aqueous MIBK per hour were distilled off via the top of the column. 600 g/h reaction solution were discharged via the bottom outlet.

Further working up of the reaction solution was carried out in accordance with Example 5 with the same results with respect to the yields.

The invention claimed is:

1. A method for the preparation of 11-pentadecen-15-olide and/or (12)-pentadecen-15-olide comprising heating 1-hydroperoxy-16-oxabicyclo[10.4.0]-hexadecane (DDP-OOH) as a starting material in the presence of a Cu(II) compound, an additive and a diluent, to produce a reaction mixture, and distilling the reaction mixture to remove an azeotrope containing water and said diluent during the heating reaction step, wherein the additive is an $\alpha,\omega$-diol or $\alpha,\omega$-amino alcohol.

2. A method according to claim 1, wherein the amount of the Cu(II) compound is 0.02 to 1.5% (mol), based on DDP-OOH.

3. A method according to claim 1, wherein the weight ratio of DDP-OOH to the total amount of the diluent used in the cleavage is in the range 1:2 to 1:7.

4. A method according to claim 1, wherein at least a portion of the diluent has been recovered from previous batches.

5. A method according to claim 1, wherein the temperature of the reaction is in the range from 80 to 100° C.

6. A method according to claim 1, wherein the additives are polyalkylene glycols.

7. A method according to claim 1, wherein the amount of additives is 0.5 to 15% (m/m), based on the DDP-OOH.

8. A method according to claim 1, wherein the water content of the DDP-OOH is in the range from 5 to 40% (m/m).

9. A method according to claim 1, wherein the method is carried out at pressures in the range from 50 to 800 mbar.

10. A method for the preparation of 1-hydroperoxy-16-oxabicyclo[10.4.0]-hexadecane (DDP-OOH) comprising reacting 13-oxabicyclo[10.4.0]hexadec-1(12)-ene (DDP) and hydrogen peroxide as starting materials by heating in the presence of acetic acid and sulphuric acid, wherein the reaction is carried out in the presence of 0.05 to 5% (mol) $H_2SO_4$, based on DDP.

11. A method according to claim 10, wherein the amount of $H_2SO_4$ is 0.1 to 3% (mol), based on DDP.

12. A method according to claim 10, wherein the amount of hydrogen peroxide is 0.8 to 1.25 molar equivalents, based on DDP.

13. A method according to claim 10, wherein after the reaction is complete, filtration and washing operations follow.

14. A method according to claim 10, wherein DDP-OOH has a water content in the range from 5 to 40% (m/m).

15. A method for the preparation of 11-pentadecen-15-olide and/or (12)-pentadecen-15-olide comprising a first step of reacting 13-oxabicyclo[10.4.0]hexadec-1(12)-ene (DDP) and hydrogen peroxide in the presence of acetic acid and 0.05 to 5% (mol) $H_2SO_4$ based on DDP to form DDP-OOH, and a second step of reacting the DDP-OOH in the presence of a Cu(II) compound, an additive, and a diluent to produce a reaction mixture, and distilling the reaction mixture to remove an azeotrope containing water and diluent during the reaction wherein the additive is an α,ω-diol or α,ω-amino alcohol.

16. A method according to claim 10, wherein the 1-hydroperoxy-16-oxabicyclo[10.4.0]-hexadecane (DDP-OOH) crystals are washed with as little water as possible in order substantially to free the crystals from acetic acid and sulfuric acid.

17. A method according to claim 16, wherein at least a portion of wash water from previous batches is used.

18. A method according to claim 16, wherein demineralized or distilled water and/or wash water from previous DDP-OOH crystal washes are used for the washing operations.

* * * * *

UNITED STATES PATENT AND TRADEMARK OFFICE
CERTIFICATE OF CORRECTION

| | | |
|---|---|---|
| PATENT NO. | : 7,183,420 B2 | Page 1 of 1 |
| APPLICATION NO. | : 10/463872 | |
| DATED | : February 27, 2007 | |
| INVENTOR(S) | : Peter Esser et al. | |

It is certified that error appears in the above-identified patent and that said Letters Patent is hereby corrected as shown below:

SPECIFICATION:

Col. 7, line, 34  change "under copper (11)" to  --under copper (II)--

Col. 7, line, 55  change "into a 6 l double-walled" to  --into a 6 liter double-walled--

Col. 8, line, 8   change "into a 6 l double-walled" to  --into a 6 liter double-walled--

Col. 8, line, 26  change "into a 6 l double-walled" to  --into a 6 liter double-walled--

Col. 9, line, 31  change "into a 6 l double-walled" to  --into a 6 liter double-walled--

Col. 9, line, 44  change "into a 6 l double-walled to  --into a 6 liter double-walled--

Col. 9, line, 64  change "vacuum with caution. distillation was discontinued and the vessel was charged with nitrogen gas."

by adding

--vacuum with caution. At a bottom temperature of 120 °C and a vacuum of approximately 60 mbar, the distillation was discontinued and the vessel was charged with nitrogen gas.--

Signed and Sealed this

Twenty-fifth Day of December, 2007

JON W. DUDAS
*Director of the United States Patent and Trademark Office*